United States Patent [19]

Mittelman

[11] Patent Number: 5,716,405
[45] Date of Patent: Feb. 10, 1998

[54] RHINOPLASTY KIT

[76] Inventor: Harry Mittelman, 23 Heather Dr., Atherton, Calif. 94027

[21] Appl. No.: 26,983

[22] Filed: Mar. 5, 1993

[51] Int. Cl.$^6$ .................................. A61F 2/18; A61F 2/54
[52] U.S. Cl. .................................. 623/10; 623/66
[58] Field of Search .................... 606/204.45, 167, 606/185, 199; 623/10, 11, 66

[56] References Cited

U.S. PATENT DOCUMENTS

| | | | |
|---|---|---|---|
| 4,436,684 | 3/1984 | White | 264/138 |
| 5,030,232 | 7/1991 | Pham | 623/10 |
| 5,112,353 | 5/1992 | Johansson et al. | 623/10 |
| 5,326,370 | 7/1994 | Love et al. | 623/2 |

Primary Examiner—Debra S. Brittingham
Attorney, Agent, or Firm—Philip Dalton

[57] ABSTRACT

A nasal plastic surgery system or kit comprises a series of templates and a series of implant cutters corresponding to the series of templates. Each of the implant cutters is configured to cut from a predetermined implant medium an implant having a peripheral form corresponding to the peripheral form of a particular one of the templates.

A template which provides a desired effect of the surgery is selected from the series of templates. An implant cutter corresponding to the selected template is then used to cut an implant having the peripheral form of the selected template.

Alternatively, preformed implants matching the series of templates may be provided to avoid cutting implants during surgery.

21 Claims, 8 Drawing Sheets

RHINOPLASTY KIT

BACKGROUND OF THE INVENTION

1. Field of the Invention

The present invention relates to methods of facial plastic and reconstructive surgery. It relates in particular to a system and method for providing grafts or implants for rhinoplasty or nasal plastic surgery.

2. Current State of the Relevant Field

A common procedure in rhinoplasty is to use implants or grafts to alter the appearance of a patient's nose. This may be done for purely aesthetic reasons, for reconstructing the nose after trauma, or in certain cases for functional reasons, for example, to facilitate breathing.

Under the collective terminology of implants or grafts fall various types of grafts, examples of which are referred to as struts, shield grafts, on-lay grafts, and dorsal grafts. Each of these types has a particular purpose in rhinoplasty, a brief description of which is presented below.

A nasal strut is usually made from cartilage, and occasionally from bone. It is made most often from autologous cartilage, for example, nasal-septal cartilage (in real time) from a patient on whom surgery is being performed and is placed between the medial crura which are part of the columella. A strut is generally rectangular in shape, and has length and width which are determined by a patient's particular situation and judgment of the surgeon. Factors to be considered are providing strength and stability to the columella, and providing projection to the external appearance of the tip of the nose.

Shield grafts and on-lay grafts are made in different shapes and sizes, depending on the cosmetic or aesthetic effect desired.

A shield graft is used for altering the appearance of the nasal tip. Typically these grafts are made from nasal-septal cartilage, conchal cartilage from the ear, or other cartilage from the patient's body. The graft may also be made from irradiated homologous cartilage from another human being. Shield grafts are generally placed at the caudal (inferior) surface of the nasal tip, to provide support to the tip, as well as to provide shape and projection.

A dorsal on-lay graft augments the dorsal surface of the nasal tip, by providing height symmetry or projection to the nasal tip. It is generally sutured into position on the nasal cartilage on which it is laid.

Whatever the type of implant or graft required, it is common practice for a surgeon to cut the implant or graft at the operating table, while surgery is being performed. This practice has certain potential risks, dependent on the skill and judgment of the surgeon. For example, under operating conditions it may be difficult for the surgeon to cut an implant which is symmetrical, or to cut two identical implants required to achieve a symmetrical cosmetic effect. A consequence of this may be a less than perfect result for the surgery.

In addition, one or more implants may not be at all suitable for use, requiring the taking of more cartilage from the patient. While cartilage is typically removed from parts of the body where the removal will not be noticeable, typically there will not be sufficient cartilage available that an extended "trial and error" approach can be used to achieve a desired effect.

There is a need for a rhinoplasty system and method which quickly produces implants of more perfect form, thereby minimizing the judgment risks of cutting an implant, and maximizing the efficiency of the method in terms of using the least amount of time and cartilage to produce the desired implant.

SUMMARY OF THE INVENTION

Among the several objects of the present invention it is desired to provide a system for quickly, reliably, reproducibly and efficiently producing grafts or implants for a surgeon engaged in rhinoplasty surgery, including functional reconstructive youthification or aesthetic surgery. It is also an object of the present invention to make rhinoplasty procedures available to more facial plastic surgeons, and to plastic surgeons and cosmetic surgeons in general.

Objects of the present invention are achieved by providing a rhinoplasty system or kit comprising a template having a peripheral form representative of a subcutaneous implant or graft for altering the appearance of a patient's nose. The system includes a graft/implant-cutter, corresponding to the template. The implant-cutter is configured to cut from a predetermined implant material an implant having substantially the peripheral form of the template.

In a preferred embodiment, the system includes a series of such templates representative of a series of implants, each having a different form, and a series of implant-cutters corresponding to the series of templates. Each of the implant-cutters is configured to cut from a predetermined material an implant having substantially the peripheral form of a particular one of the series of templates. An implant-cutter is preferably provided with a handle, for holding the implant-cutter while cutting an implant.

In one aspect of the present invention, an implant cutter includes a blade portion comprising a closed band of a sharpenable material. At one end of the blade portion is a cutting edge. The cutting edge generally defines a cutting plane, and is arranged to correspond to the peripheral form of a particular one of the templates.

In another aspect of the present invention, each of the impact cutters in the series of implant-cutters are configured such that any one of the impact cutters may be removably attached to a common handle. The handle and the impact cutters may be configured such that the handle extends perpendicularly from the cutting plane when an implant-cutter is attached thereto. The handle and the cutters may also be configured such that the handle extends parallel to the cutting plane when a implant-cutter is attached thereto. In this latter configuration, the handle may also include means for ejecting an implant from a implant-cutter attached thereto, should the implant be trapped in the impact cutter after cutting.

In yet another aspect of the present invention, the system may include bevelling means for providing a bevelled edge on an implant.

In still another aspect of the present invention a template may be provided with a series of apertures extending therethrough for indicating locations where an corresponding implant may be optimally sutured in position on underlying cartilage of a patient's nose. A pick tool extendable through the apertures in the template may be used to provide perforations in an implant for optimal suture locations.

In another embodiment of the present invention a rhinoplasty system includes at least one template having a peripheral form representative of an implant for altering the appearance of a patient's nose, and at least one implant corresponding to the template and having substantially the peripheral form of the template. Preferably such a system includes a series of templates representative of a series of implants, and includes a series of implants corresponding to the series of templates, each of the implants having substantially the peripheral form of a particular one of the series of templates.

In one embodiment of a surgical method using the system of the present invention, a series of templates representative of implants having different forms and sizes is provided, and a series of implant-cutters corresponding to the series of templates is provided. Each of the impact cutters is configured to cut from a predetermined implant medium an implant having a peripheral form corresponding to the peripheral form of a particular one of the templates.

A template which provides a desired cosmetic, functional, or structural effect of the surgery is selected from the series of templates. An implant-cutter corresponding to the selected template is selected from the series of impact cutters. The selected implant-cutter is then used to cut from the implant medium an implant having the peripheral form of the selected template.

One procedure for selecting the template comprises choosing from the series of templates a group of templates representative of implants which may provide the desired effect. A template selected from the group of templates is then temporarily set in position on a patient's nose and the effect of the template is evaluated. This procedure is repeated, using different templates from the group, until a template is selected which provides an effect closest the effect desired by the surgeon.

In another embodiment of a surgical method using a system in accordance with the present invention, comprises providing a series of templates representative of subcutaneous implants/grafts having different shapes and sizes, each of the templates having a peripheral form and providing a series of implants, with each of the implants/grafts corresponding in peripheral form to a particular one of the series of templates;

A template which provides a desired cosmetic, functional, or structural effect of the surgery is selected from the series of templates. An identical cartilage (or other material) graft can then be created with the corresponding implant/graft cutter. If an implant is desired, an implant corresponding to the selected template is selected from the series of implants. Surgery is completed using the selected graft or implant. The template may be selected in accordance with the template selection procedure described above.

BRIEF DESCRIPTION OF THE DRAWINGS

The accompanying drawings, which are incorporated in and constitute a part of the specification, schematically illustrate a preferred embodiment of the invention and, together with the general description given above and the detailed description of the preferred embodiment given below, serve to explain the principles of the invention.

DETAILED DESCRIPTION OF THE PREFERRED EMBODIMENT(S)

Throughout the description set forth below references is made to grafts and implants. Grafts are usually understood in the art to comprise implants of human tissue. The grafts are usually made from the patients own tissues, but may be occasionally made from tissues of other human beings. The term implant may be applied specifically to implants made from synthetic materials such as alloplastic materials, but it may also be convenient to collectively define both grafts of human tissue and synthetic material implants. It is intended that the term implant as used in the appended claims collectively define implants of synthetic material and grafts or implants of human tissue.

FIGS. 1 through 5 illustrate various types of implant or graft templates in accordance with the present invention. FIGS 1A and 1B depict one form 20 of a strut implant which has the generally rectangular peripheral form shown in FIG. 1A and is uniformly relatively thin, as illustrated in FIG. 1B.

Figures 1A, 1B:
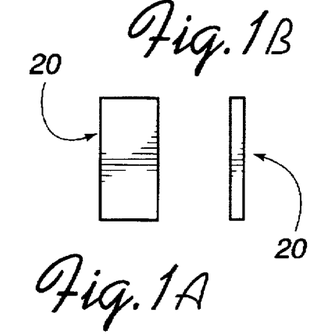
FIGS. 1A and 1B are, respectively, plan and elevation views which schematically illustrate a strut template in accordance with the present invention.

Such a template may have a length between about 0.5 and 2.5 centimeters (cm), a width between about 0.1 cm and 0.9 cm, and a thickness between about 0.1 cm and 0.5 cm.

Figure 2A:
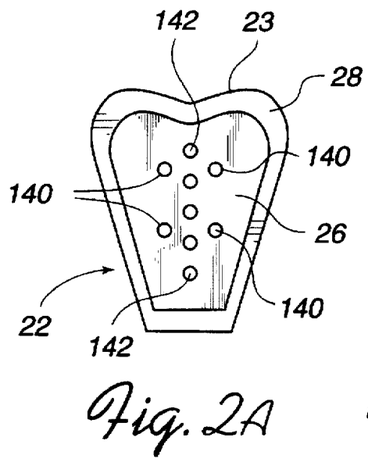
FIGS. 2A and 2B are, respectively, plan and elevation views schematically illustrating one form of a nasal-tip shield graft template in accordance with the present invention, the template including perforations for locating suture sites on an implant, and bevelled edges.
Figure 2B:
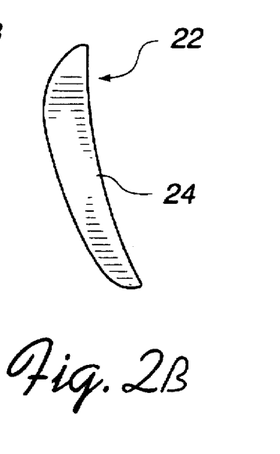
Figure 2C:
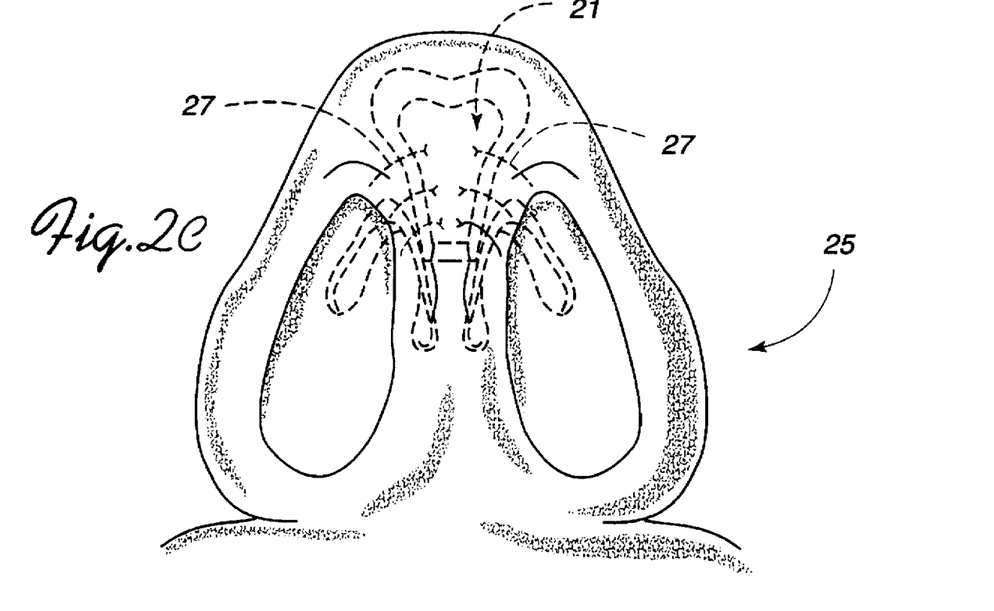
FIGS. 2C and 2D are pictorial views schematically illustrating a nasal-tip shield graft, corresponding generally in peripheral form to the template of FIGS. 2A and B, sutured in position on a patients nose.
Figure 2D:
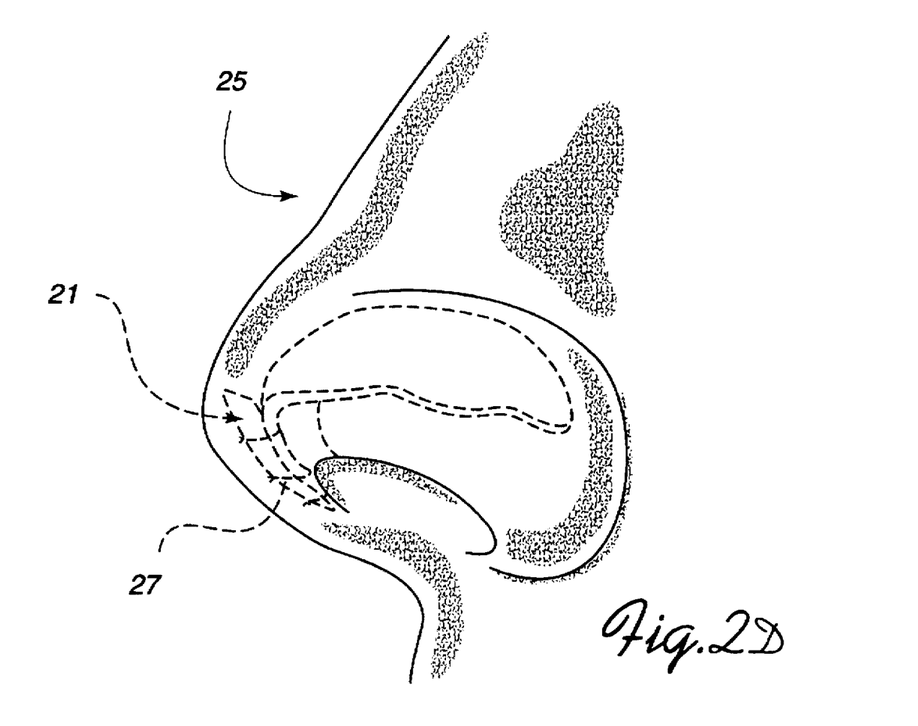

A nasal tip or shield graft implant template 22 is illustrated in FIGS. 2A and 2B. Such an template 22 generally has the shield-like or heart-like shape illustrated in FIG. 2A. Such a template may have a non-uniform thickness, as illustrated in FIG. 2B. The thickness is preferably greater toward the middle 22A of the template. The template preferably incorporates a slightly curved lower surface 24 generally corresponding to the inferior surface of a nasal columella. FIGS. 2C and 2D illustrate a graft 21 generally corresponding in peripheral form to template 22 and held in position on a patient's nose 25 by sutures 27.

Preferably, the shield graft template 22 includes a bevelled edge portion 28 around its entire periphery. It is desirable that such a bevelled edge be provided to the implant corresponding to the template so that the implant is not noticeable when it is in position under the skin of a patient's nose. Methods for providing such a bevelled edge in a finished implant are discussed in detail below. Such templates usually have a height between about 1.0 cm and 2.0 cm, an upper width between about 0.7 cm and 2.0 cm, a lower width between about 0.3 cm and 1.2 cm, and a thickness between about 0.1 cm and 0.6 cm.

Figure 3A:
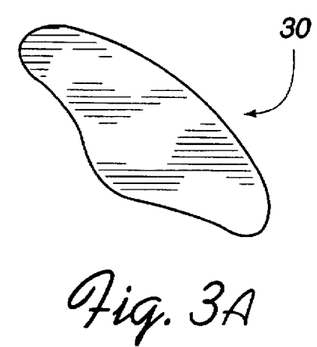
FIGS. 3A and 3B are plan views schematically illustrating respectively right and left crural on-lay graft templates in accordance with the present invention.
Figure 3B:
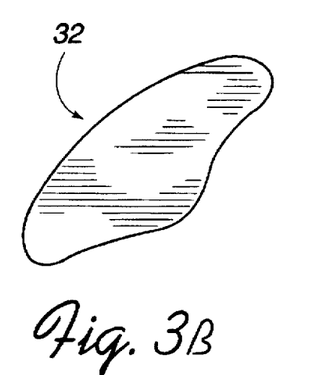
Figure 4A:
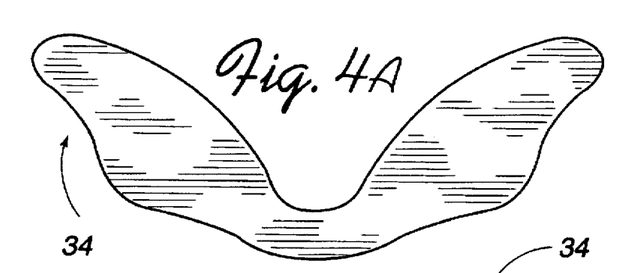
FIGS. 4A and 4B are, respectively, plan and elevation views schematically illustrating a combined, one piece, crural connecting on-lay graft template in accordance with the present invention.
Figure 4B:
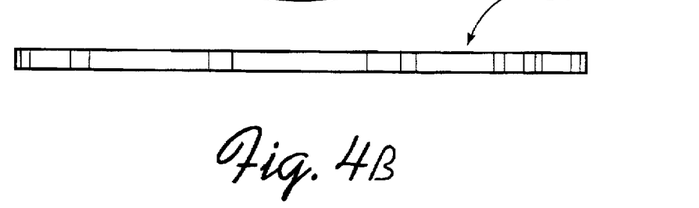

FIGS. 3A and 3B illustrate templates 30 and 32, representing respectively right and left crural on-lay grafts or implants. In FIGS. 4A and 4B respectively plan and elevation views of a combined right and left crural-connecting on-lay graft template 34, having a butterfly shaped peripheral form, are illustrated. Crural and combined crural-connecting templates are preferably relatively thin, as exemplified in FIG. 4B. They are preferably flexible, for following the nasal contour in the lateral crural area of the nose, where contour changes may be relatively complex. Grafts or implants corresponding to such templates are sometimes applied as two or more layers having the same or different form. This allows a particular desired implant shape to be built up, rather than carved from a single piece of implant material.

Figure 5:
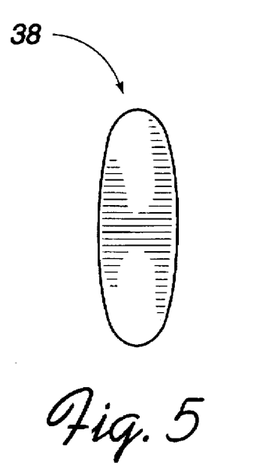
FIG. 5 is a plan view schematically illustrating a dorsal on-lay graft template in accordance with the present invention.

Finally, but not exhaustively, FIG. 5 is a plan view of a dorsal on-lay graft template 38 having a generally elliptical peripheral form. A dorsal on-lay graft typically is applied on the nasal dorsum for altering the line of the nose.

According to the present invention, an implant template, whatever its peripheral form or size, has corresponding to it an implant cutter. As summarized above a preferred embodiment of the invention has a series of templates of different shapes and sizes, each template having an implant cutter corresponding thereto. An implant cutter is configured to cut from a selected implant material an implant having substantially the same peripheral form as the template to which the implant cutter corresponds. The thickness of the implant will be determined, in general, from the material or medium from which it is cut, or the judgement of the surgeon.

It should be noted at this point in the present discussion that it is an object of the present invention to provide implants which resemble the templates from which the grafts are produced, to the maximum extent possible. Because of this congruency, separate drawings for the templates and the corresponding implants are not necessary for purposes of describing the principles and scope of the present invention. Accordingly, drawings are provided only for the templates. These drawings may be used interchangeably, without risk of confusion, for determining the form of corresponding implants.

Figure 6:
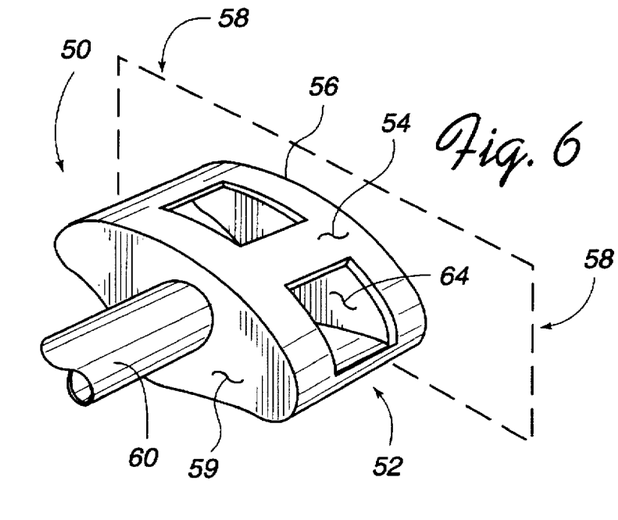
FIG. 6 is a perspective view schematically illustrating one form of an implant-cutter in accordance with the present invention.

Referring now to FIG. 6, there is shown an implant cutter 50 corresponding to the crural on-lay graft template 34 depicted in FIG. 4A. Implant cutter 50 includes a blade portion or head 52 comprising a closed band 54 of a sharpenable material. The material of band 54 is preferably a metal such as surgical steel which is capable of accepting and maintaining a sharp edge 56 over a long period of use. The band 54 may also be formed from a softer metal such as aluminum, or even from a plastic, for example, to reduce the cost of the cutter. A lesser ability of such softer materials to maintain a sharp edge may be acceptable, particularly if the reduced cost allows a wider selection of templates and corresponding implant-cutters.

Figures 7, 8:
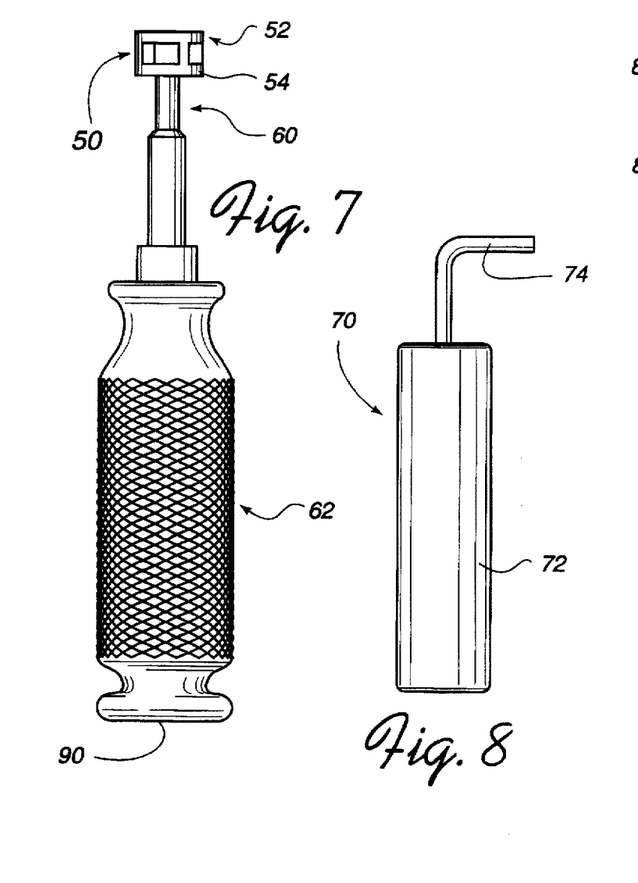
FIG. 7 is an elevation view schematically illustrating the implant cutter of FIG. 6, removably attached to a handle.
FIG. 8 is an elevation view schematically illustrating a probe device for ejecting a trapped implant from the implant cutter of FIG. 6.

At one end of head 52, band 54 has a cutting edge 56 generally defining a cutting plane indicated in phantom by line 58. Cutting edge 56 is configured to correspond to the peripheral form (shape and size) of the template to which cutter 50 corresponds. At the other end of band 54 is an end-wall 59. A shaft 60 attached to end-wall 59 may be used to fixedly attach implant-cutter 50 to a handle 62 as illustrated in FIG. 7. Methods of removably attaching such an implant-cutter to a handle are also described below.

It is intended that an implant cutter of the type exemplified by cutter 50 be used to cut shapes, from implant materials or media, generally in the manner in which closed-band-type "cookie" cutters are used to cut dough or pastry shapes. After being cut in such a manner, the implant may be stuck or trapped in the implant-cutter. To remove a trapped implant from cutter 50 without damaging the implant, one or more openings 64 are provided through the sides of the hollow band 54. A probe device such as 70, FIG. 8, can be inserted through an opening for removing or ejecting the trapped implant.

The illustrated probe 70 includes a handle 72 having a right-angled probe tip 74 having dimensions sufficiently small that it may be inserted through opening 64 in band 54. Those skilled in the art may envision several different types of probe device without departing from the general principle of probe device 70.

As discussed above, a preferred embodiment of the invention includes a series of templates of different shapes and sizes, each template having an implant cutter corresponding thereto. It is preferable, for reducing the size and weight of a set of implant cutters, that each cutter not require a fixedly attached handle, but rather that the implant cutters in a given series be removably attachable to a common handle.

Figure 9:
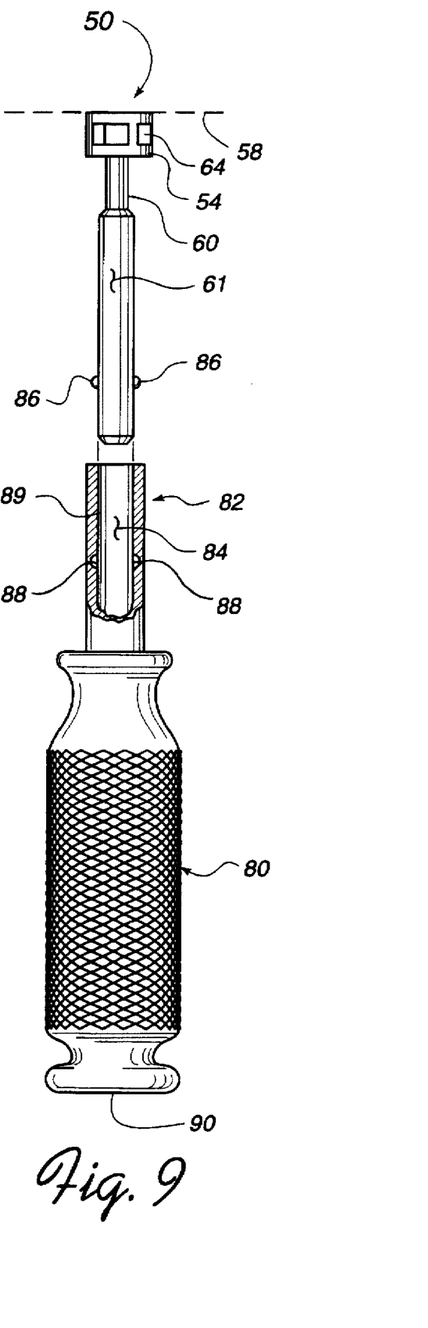
FIG. 9 is an elevation view schematically illustrating one method of removably attaching the implant-cutter of FIG. 6 to a handle.

FIG. 9 depicts one approach for removably attaching implant cutter 50 to a handle. Here, a handle 80 includes a socket portion 82 having a generally cylindrical bore 84. Handle 80 is configured such that it extends generally perpendicular from cutting plane 58 when an implant cutter is attached thereto. Shaft 60 attached to implant-cutter 50 includes a plug portion 61 configured to fit snugly in bore 84. A well known ball-indent arrangement, depicted in FIG. 9 by balls 86 on shaft 60 and indents 88 on the interior wall 89 of bore 84, may be used to secure implant cutter 50 to handle 80 during cutting. Preferably, handle 80 is provided with a flattened end 90. Depending on which implant material is being cut, and on the sharpness of the cutting edge of impact cuter 50, it may be necessary to assist the cutting process by striking or tapping the end 90 of the handle 80 with a mallet or the like (not shown). Flat end 90 provides a convenient striking surface for a mallet.

Figures 10, 11:
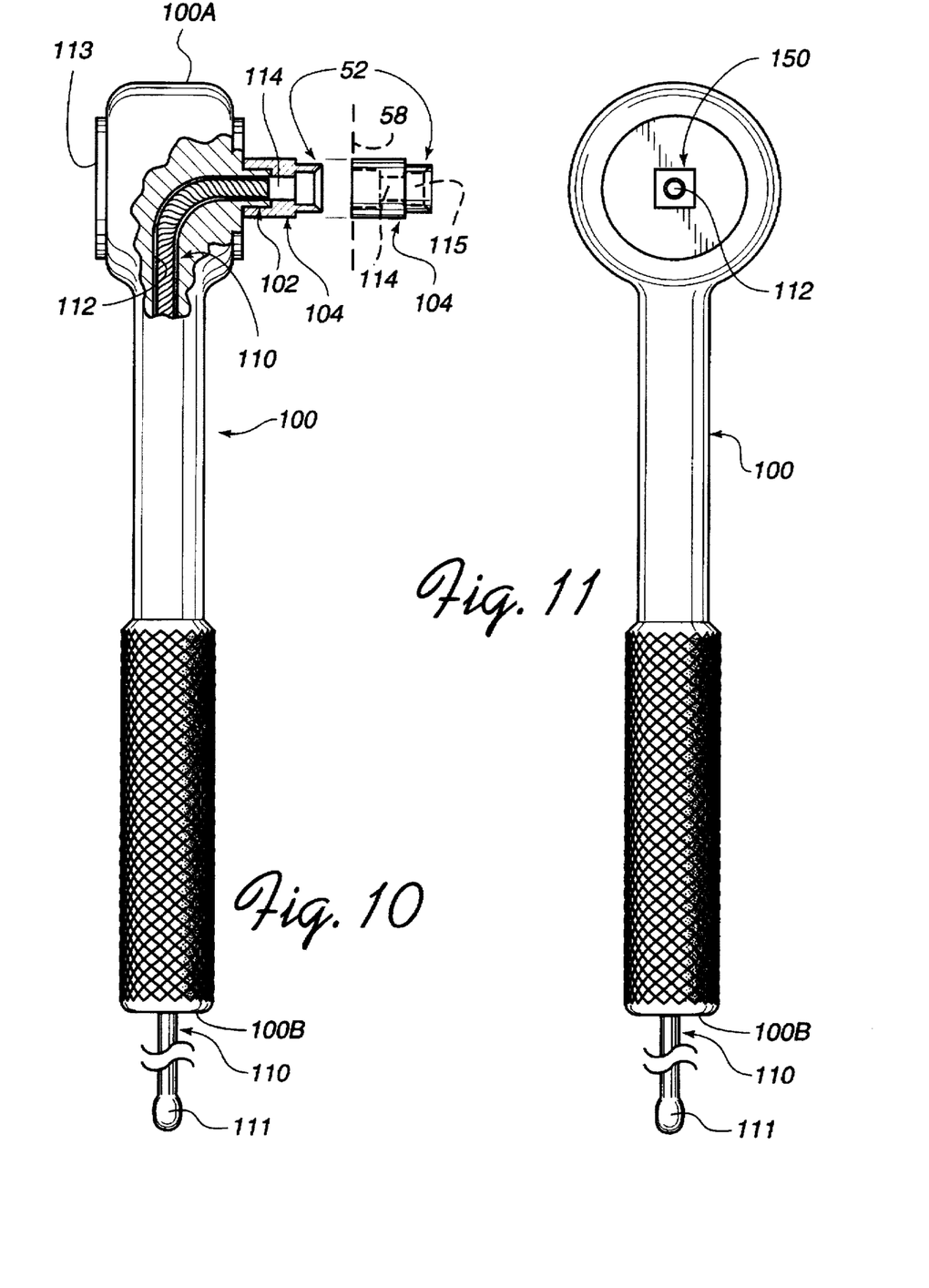
FIG. 10 is a side elevation, partially cut away, schematically illustrating another approach for removably attaching the implant-cutter of FIG. 6 to a handle, and illustrating means, located in the handle, for ejecting an implant which may be trapped in an implant-cutter attached thereto.
FIGS. 11 and 12 are top and bottom plan views of the handle of FIG. 10.
Figure 12:
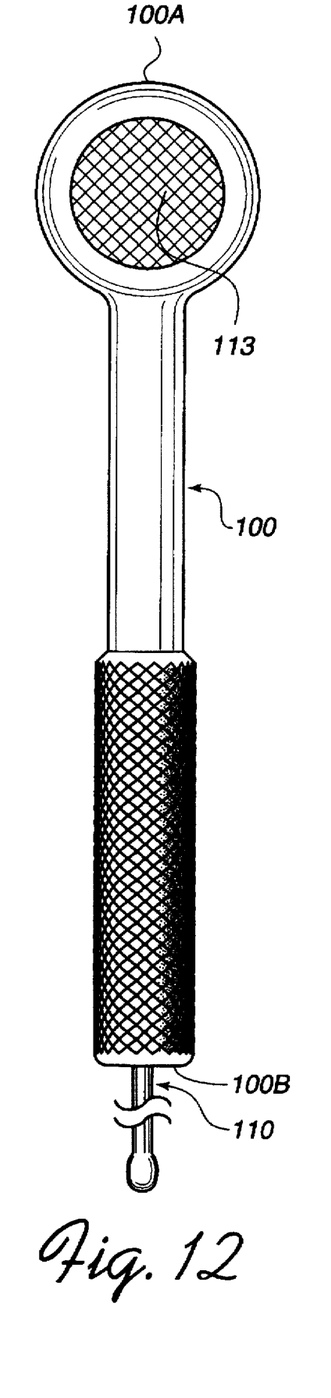

FIGS. 10, 11, and 12 show another approach for removably attaching an implant cutter such as 50 to a handle. FIG. 10 illustrates an elongated handle 100 having, at one end 100A thereof, a plug portion 102 extending generally perpendicularly therefrom. Plug portion 102 preferably has a generally square cross section and is configured to mate with a socket portion 104 of implant cutter 50. (In this embodiment, the shaft or plug 60 of implant cutter 50, FIG. 6, is formed as the socket 104, FIG. 10.) Implant cutter 50 may be retained in position on plug portion 102 by a ball-indent arrangement, similar to the arrangement described above. A description of this arrangement has been omitted from FIG. 10 for clarity.

As discussed above, implant cutting may require impact assistance, provided, for example, by a blow from a mallet or the like. To this end, it is preferable to that handle 100 have a generally flat, frictional striking surface 113, FIGS. 10 and 12. The frictional characteristics of the striking surface are provided by xy striations which prevent the mallet from glancing off the striking surface. A similar frictional surface may be used on handle end 90, FIGS. 7 and 9.

Continuing with reference to FIG. 10, handle 100 may include an arrangement for ejecting an implant which is trapped in implant-cutter 50 attached thereto. In an illustrative example, the impact ejecting arrangement may comprise a flexible plunger arrangement 110 extending through handle 100. Plunger 110 is extendable and retractable through an aperture 112 in plug portion 102 of handle 100, by providing a push-pull action on plunger end 111 extending from end 100B of handle 100. The push pull action on plunger 110 is indicated by arrow A in FIG. 10. Aperture 112 of plug portion 102 is aligned with necked aperture 114 extending from socket portion 104 into blade portion 52 of implant cutter 50. This permits plunger 110 to be extended through plug portion 102 and into blade portion 50 against the neck 115 for ejecting a trapped implant.

Figure 13:
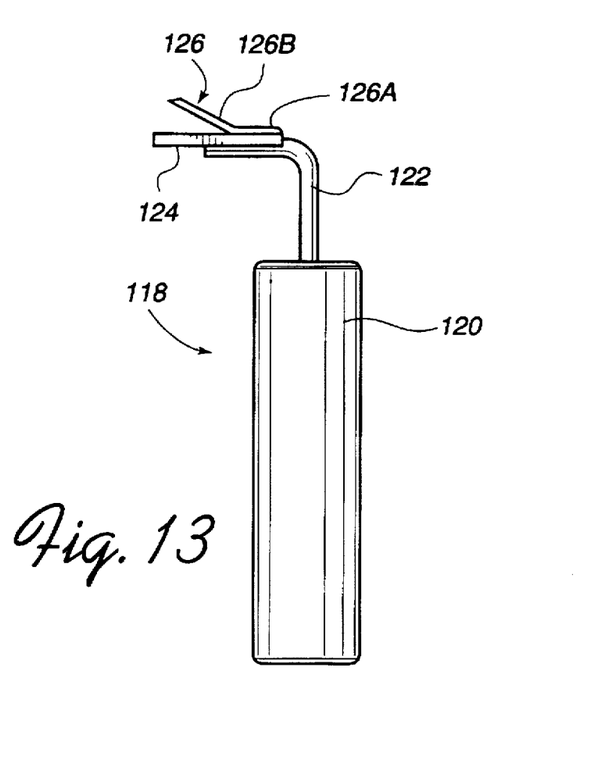
FIG. 13 is an elevation view schematically illustrating a bevelling device in accordance with the present invention for providing a bevelled edge on an implant.
Figure 14:
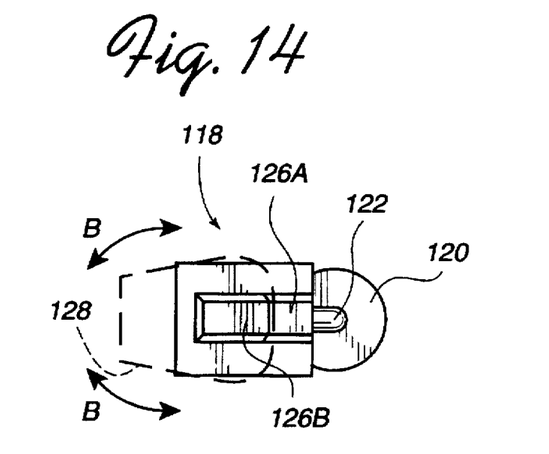
FIG. 14 is a plan view of the bevelling device of FIG. 13.

As discussed above, it is preferable that certain types of implants such as nasal-tip or shield grafts, be provided with a bevelled edge or periphery. One approach for providing such a bevelled edge is illustrated in FIGS. 13 and 14. Here, an edge bevelling device 118 comprises a handle 120 having a right-angled bracket 122 mounted to or formed integrally with handle 120. Mounted on the right-angled bracket 122 is generally flat platform 124, to which a blade 126 is mounted at one end 126A thereof. An opposite end 126B of blade 126 extends at an angle theta, preferably between about thirty and forty-five degrees, from platform 124. An implant to be bevelled (shown in phantom in FIG. 14 by dotted line 128 indicating the edge or periphery of the implant) is placed on platform 124 with edge 128 in contact with blade 126. The edge of the implant can then be bevelled by manually rotating the implant around the platform, as indicated by arrow B, while maintaining edge 128 in contact with blade 126 so that the blade shaves the implant edge to a bevel characterized by an angle approximating the blade orientation angle theta, FIG. 13.

Figure 15:
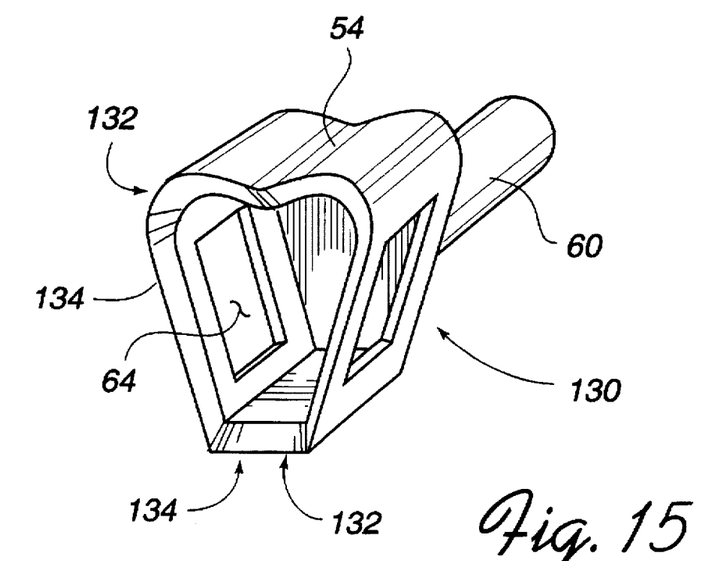
FIG. 15 is a perspective view schematically illustrating a nasal-tip implant-cutter in accordance with the present invention.

A bevelled edge can also be formed in an implant by providing a bevelled cutting edge to an implant-cutter. This is illustrated in FIG. 15 with reference to a nasal tip implant-cutter 130, in which cutting edge 132 thereof includes an inwardly bevelled portion 134 extending peripherally around the cutting edge.

Bevelled edges are preferred on implants of the nasal tip or dorsal type. Bevelled edges are generally not required on crural on-lay type implants which are generally relatively thin, although such implants may benefit from some degree of edge bevelling.

Those familiar with rhinoplasty methods will be aware that certain implants, particularly struts, nasal-tip or shield grafts and dorsal grafts, are preferably sutured to adjacent nasal cartilage or soft tissue to maintain their intended position, that is, for stability. It is particularly important that sutures in nasal-tip and dorsal grafts be placed in and maintained in precise location for ensuring symmetry and stability of the graft.

The template feature of the present invention provides means for optimally and accurately providing suture locations in an implant for a surgeon desiring such a feature. Referring now to FIGS. 2A and 2B, template 22 includes an array of apertures 140 which can be used to control the placement of sutures in the associated implant. Typically, but not exclusively, four sutures are required, disposed generally at the locations 140. Also, it has been determined that additional stability may be achieved by providing additional apertures or perforations in the implant which are not filled by sutures. Instead, scar tissue may grow through these apertures, providing additional stability for the implant. The additional apertures are preferably located along the center of the implant, as illustrated by apertures 142 in FIG. 2A. This scar tissue aperture method has been found to be effective because the scar tissue bond is sufficiently strong to provide additional stability to an in-place implant, but not so strong that it inhibits later removal of the implant should that be required.

Figure 16:
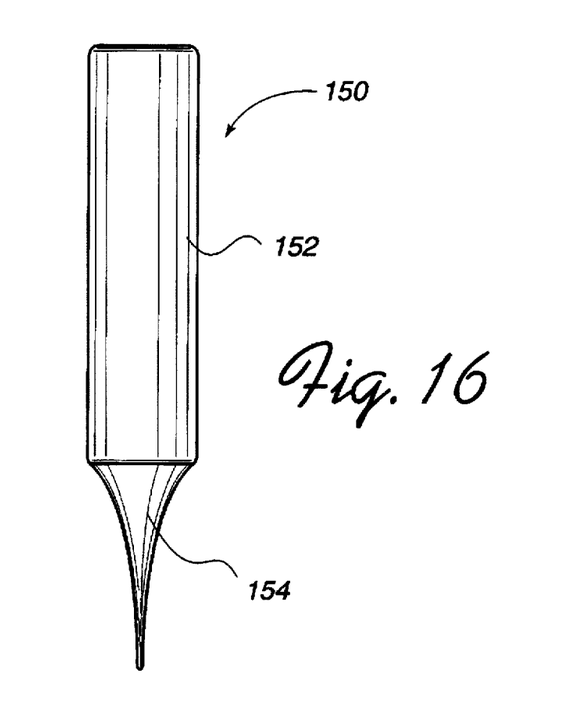
FIG. 16 is an elevation view schematically illustrating a suture pick device cooperative with the template of FIG. 2A for providing suture perforations in an implant.

FIG. 16 illustrates a pick device 150 including a handle 152 and a pick tip 154, which may be used to make suture and scar tissue perforations in an implant generated from the template, by aligning the template with the implant and punching the pick tip 154 through the template and the implant, i.e., using the template apertures as a pattern.

Certain graft types, such as crural on-lay grafts are not necessarily routinely sutured in position. When such grafts are sutured in position, the location of suture sites may not be as important as for nasal-tip or dorsal grafts. It is intended that templates for such grafts be available with and without perforations, and that the decision to use one or the other be left to the judgment of the surgeon.

Continuing now with a discussion of preferred materials for templates in accordance with the present invention, a material for nasal tip and strut templates is preferably a material which will provide a firm template able to maintain its shape and form after continual use. A template is preferably also sufficiently temperature resistant that it may withstand repeated sterilization. While such templates could be made from stainless steel or some other corrosion resistant metal, it is preferable, particularly for a nasal-tip or shield graft template, that the template have some degree of flexibility to allow the template to conform to a particular patient's nasal-tip curvature. Hard moldable plastic materials, such as nylon or polyurethane, are a group of materials which provide the hardness, flexibility and heat resistance properties required for templates.

On-lay templates such as crural and crural-connecting implant templates are relatively thin and are required to be sufficiently flexible to conform to a wide variety of shapes and curvatures. A suitable material for such templates is a silastic type silicone containing elastomer or softer plastic.

Common implant and graft materials include autologous cartilage, homologous cartilage, and bone.

Generally, materials suitable for template fabrication include the group of materials which consists of metals, hard and soft plastics, silicone-containing elastomers, and fabric including fluorinated-hydrocarbon-polymer, such as fabric sold under the trade name GORE-TEX.

Suitable implant materials include silicone-containing elastomers, fabric including fluorinated-hydrocarbonpolymer, animal and human-like collagen, collagen compounds, vicryl mesh, GORE-TEX, polyimid mesh and hyaluronic acid compounds.

The foregoing description of the present invention has been given in terms of cutting grafts or implants during a surgical procedure. As discussed cutting grafts or implants during the surgical procedure is usual, particularly when grafts or implants are cut from human tissue. It will, however, be evident to those familiar with rhinoplasty methods that, particularly for implants of synthetic materials, it may be convenient to for a surgeon to have available a series of pre-cut or pre-formed implants. Accordingly, in an alternative embodiment of the present invention a surgeon has available a series of pre-formed implants of different peripheral forms and sizes each thereof corresponding to a particular one of a series of templates of different peripheral forms and sizes. Availability of pre-formed implants may be effective in speeding the surgical procedure or in reducing wastage of implant material which may be incurred during on site cutting. This may be particularly important with implant materials which are expensive materials and which are expensive to produce.

Figure 17:
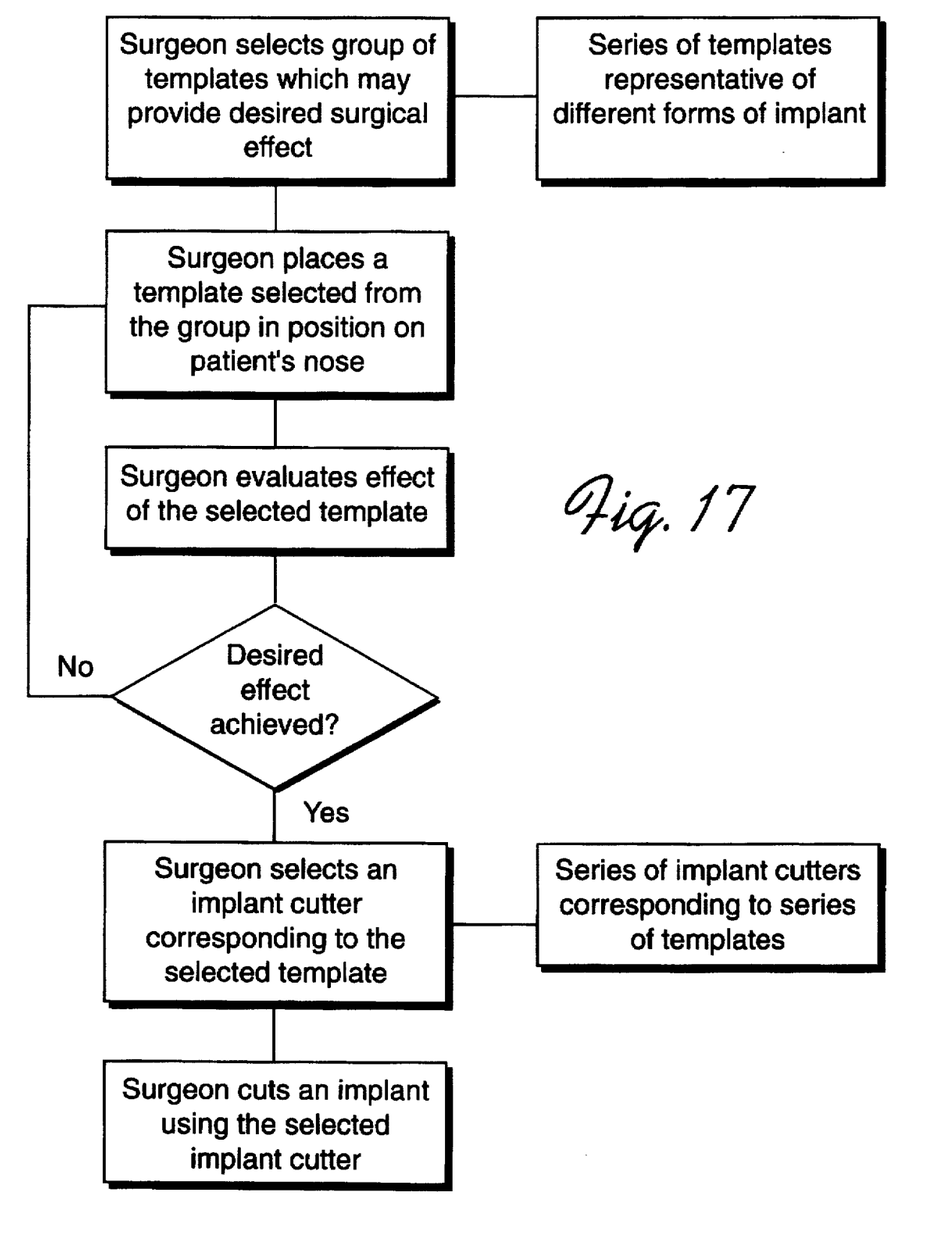
FIG. 17 is a flow chart summarizing one method of practicing my present method of preparing and placing implants.

In summary, a system and method for providing grafts and implants in nasal plastic surgery has been described. Referring now to the flow chart shown in FIG. 17, a surgeon may select from a series of templates representative of a series of implants or grafts of different shapes and sizes a group of templates which may provide a desired surgical effect on a patient's nose. The surgeon then temporarily holds against the patient's nose a template selected from the group of templates which may produce the desired effect. This procedure may be repeated using different templates from the group until a template is selected which provides an effect closest to the desired effect. The surgeon then selects, from a series of implant cutters corresponding to the series of templates, an implant cutter corresponding to the selected template, and uses this implant cutter to cut from a predetermined material an implant or graft having the form of the selected template. The surgeon may repeat the above process as required for different implants which are to be inserted during the rhinoplasty procedure. The surgeon completes the surgery, either after fabricating the implant or a group of different implants.

Figure 18:
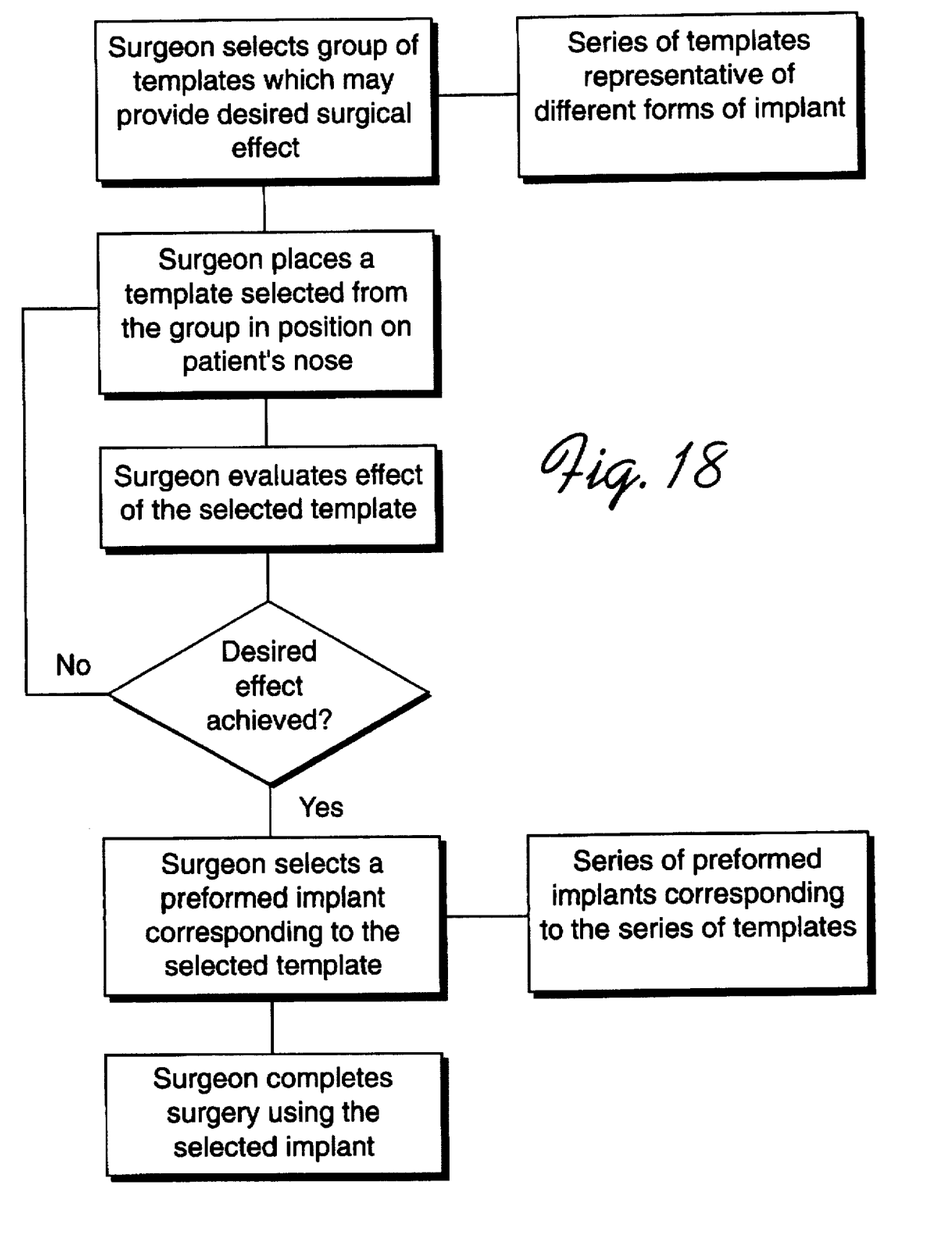
FIG. 18 is a flow chart summarizing another method of practicing my present method of preparing and placing implants.

Referring now to the flow chart shown in FIG. 18, in a method using the above described alternative embodiment of my rhinoplasty system, a surgeon may select from a series of templates representative of a series of implants or grafts of different shapes and sizes a group of templates which may provide a desired surgical effect on a patient's nose. The surgeon then temporarily holds against the patient's nose a template selected from the group of templates which may produce the desired effect. This procedure may be repeated using different templates from the group until a template is selected which provides an effect closest to the desired effect. The surgeon then selects, from a series of pre-formed implants, each thereof corresponding to a particular one of the series of templates, or an implant cutter corresponding to the selected template, and uses this implant to complete the rhinoplasty procedure.

Conveniently, the components of my rhinoplasty system can be located in a kitbox for convenient storage, carrying and use, preferably with the various system components being located in selected compartments, much in the manner of a tool kit comprising a compartmented tool box and tools.

The present invention provides a system whereby a surgeon engaged in rhinoplasty surgery, including functional reconstructive youthification or aesthetic surgery, may more quickly, more reliably, more reproducibly, and more efficiently, produce grafts or implants for use in the surgery. The invention reduces the requirement for particular manual skill and judgment on the part of the surgeon together with the risks attendant thereto. Because of this, the present invention may make rhinoplasty procedures available to more facial plastic surgeons, and to plastic surgeons and cosmetic surgeons in general. The use of templates to assess cosmetic effects of surgery is helpful in providing for improved cosmetic results of the surgery. The use of templates also provides a means for objectively archiving a surgical procedure, and for providing more objective operative reports, both written and diagrammatic.

The present invention has been described in terms of a preferred embodiment and a number of other embodiments. The invention however is not limited to the embodiments described and depicted. Rather, the scope of the invention is defined by the appended claims.

What is claimed is:

1. A system for rhinoplasty, comprising:
   at least one template, the template having a peripheral shape representative of an implant for altering the appearance of a patient's nose, and wherein the template is representative of an implant selected from the group consisting of nasal struts, shield grafts, nasal-tip grafts, dorsal on-lay grafts, lateral-crural on-lay grafts, and combined crural-connecting on-lay grafts; and
   at least one implant cutter, the implant cutter corresponding to the template and configured to cut from a predetermined material an implant having substantially the peripheral shape of the template.

2. The system of claim 1 wherein the implant cutter is attached to a handle.

3. The system of claim 1 including a series of templates representative of a series of implants, and including a series of implant cutters corresponding to the series of templates, each of the implant cutters being configured to cut from a selected implant material an implant having substantially the peripheral shape of a particular one of the series of templates.

4. The system of claim 3 wherein each of the implant-cutters includes a blade portion comprising a closed band of a sharpenable material, the blade portion having at one end thereof a cutting edge, the cutting edge generally defining a cutting plane, and the cutting edge arranged to correspond to the peripheral shape of a particular one of the templates.

5. The system of claim 4 further including at least one handle, and wherein the handle and the implant cutters are configured to removably attach the implant cutters to the handle.

6. The system of claim 5 wherein the handle includes means for ejecting an implant from an implant cutter attached thereto.

7. The system of claim 6 wherein the handle extends generally parallel to a predetermined cutting plane when a implant-cutter is attached thereto.

8. The system of claim 7 wherein the handle includes at one end thereof a plug member extending generally perpendicular therefrom, for receiving a implant cutter.

9. The system of claim 8 wherein the implant ejection means includes flexible plunger means, the plunger means extending axially through the handle and extendable through a first aperture in the plug member.

10. The system of claim 9 wherein each of the implant-cutters further includes a socket portion for removably attaching the implant-cutter to the plug member, the socket portion including a second aperture extending therethrough into the blade member, the second aperture cooperative with the first aperture in the plug member for receiving the plunger means.

11. The system of claim 5 wherein the handle extends generally perpendicular to the cutting plane when a implant-cutter is attached thereto.

12. The system of claim 11 wherein the band of sharp-enable material includes at least one opening extending therethrough.

13. The system of claim 12 further including a probe member configured for extending through the opening for ejecting an implant trapped in the blade member after cutting.

14. The system of claim 13 wherein the implant cutter includes a plug member and the handle has a socket therein, the socket being cooperative with the plug member for removably attaching the cutting member from to the handle.

15. The system of claim 1 wherein the template includes a first plurality of apertures extending therethrough for defining points on the implant at which the implant may be sutured in position on the patient's nose.

16. The system of claim 15 further including pick means extendable through the apertures in the template for providing a perforation in which a suture is to be placed for holding the implant in position.

17. The system of claim 15 wherein the template further includes a second plurality of apertures extending therethrough for defining points on an implant where perforations are to be made in the implant for allowing the growth of scar tissue therethrough.

18. The system of claim 1 further including a device for forming a bevelled edge around the implant.

19. The system of claim 18 wherein the edge-bevelling means includes a generally flat platform, and a blade member, the blade member attached to one end thereof to the platform and extending at a predetermined angle therefrom, whereby the implant may be placed in contact with the blade member and moved about the platform such that the blade member cuts a bevelled edge on the implant.

20. The system of claim 19 further including a handle attached to the edge-bevelling means.

21. The system of claim 1 wherein the template is formed from a material selected from the group consisting of metals, hard and soft plastics, silicone-containing elastomers, and fabric containing fluorinated-hydrocarbon-polymer.

* * * * *